US009897350B2

(12) United States Patent
Longsworth

(10) Patent No.: US 9,897,350 B2
(45) Date of Patent: Feb. 20, 2018

(54) MRI COOL DOWN APPARATUS

(71) Applicant: Sumitomo (SHI) Cryogenics of America, Inc., Allentown, PA (US)

(72) Inventor: Ralph Longsworth, Allentown, PA (US)

(73) Assignee: SUMITOMO (SHI) CRYOGENICS OF AMERICA INC., Allentown, PA (US)

( * ) Notice: Subject to any disclaimer, the term of this patent is extended or adjusted under 35 U.S.C. 154(b) by 0 days.

(21) Appl. No.: 14/655,853

(22) PCT Filed: Jan. 2, 2014

(86) PCT No.: PCT/US2014/010054
§ 371 (c)(1),
(2) Date: Jun. 26, 2015

(87) PCT Pub. No.: WO2014/109941
PCT Pub. Date: Jul. 17, 2014

(65) Prior Publication Data
US 2015/0354865 A1 Dec. 10, 2015

Related U.S. Application Data

(60) Provisional application No. 61/751,457, filed on Jan. 11, 2013.

(51) Int. Cl.
*F25B 9/00* (2006.01)
*F25B 45/00* (2006.01)
(Continued)

(52) U.S. Cl.
CPC ............ *F25B 19/005* (2013.01); *A61B 5/055* (2013.01); *F25B 9/14* (2013.01); *F25D 19/00* (2013.01);
(Continued)

(58) Field of Classification Search
CPC .. F25J 1/02; F25J 1/0205; F25J 1/0261; F25J 1/0268; F25J 1/0007; F25J 2270/30;
(Continued)

(56) References Cited

U.S. PATENT DOCUMENTS 4,484,458 A 11/1984 Longsworth
5,193,348 A * 3/1993 Schnapper ............... F25B 9/00
324/248

(Continued)

FOREIGN PATENT DOCUMENTS

CN 1892931 A 1/2007
CN 101109583 A 1/2008
(Continued)

OTHER PUBLICATIONS

International Search Report and Written Opinion dated Apr. 18, 2014, from the corresponding PCT/US2014/010054.
(Continued)

*Primary Examiner* — Frantz Jules
*Assistant Examiner* — Erik Mendoza-Wilkenfe
(74) *Attorney, Agent, or Firm* — Katten Muchin Rosenman LLP

(57) ABSTRACT

A means and a method to cool down an MRI magnet, in a cryostat that is designed for a maximum pressure of about 0.2 MPa, are described which use cold helium output from a Brayton cycle refrigerator at a pressure of about 0.8 MPa to exchange heat with helium in the MRI cryostat in a coupling heat exchanger that is located removeably in or proximate the neck tube of the MRI cryostat. A circulator drives helium from the MRI cryostat through the coupling heat exchanger.

8 Claims, 3 Drawing Sheets

(51) Int. Cl.
*F25B 19/00* (2006.01)
*A61B 5/055* (2006.01)
*G01R 33/38* (2006.01)
*F25D 19/00* (2006.01)
*F25B 9/14* (2006.01)
*G01R 33/3815* (2006.01)

(52) U.S. Cl.
CPC ...... *G01R 33/3804* (2013.01); *F25B 2400/17* (2013.01); *G01R 33/3815* (2013.01)

(58) Field of Classification Search
CPC ................. F25B 45/00; F25B 2345/00; F25B 2345/001; F25B 9/00; F25B 9/06; F25B 9/12; F25B 9/14; F17C 2227/0353; F17C 2227/0372; F17C 2227/0337; F17C 2227/0339; F17C 2227/0313
See application file for complete search history.

(56) References Cited

U.S. PATENT DOCUMENTS

| | | | |
|---|---|---|---|
| 5,461,873 A | | 10/1995 | Longsworth |
| 5,687,574 A | * | 11/1997 | Longsworth ............. B01D 8/00 417/901 |
| 6,347,522 B1 | | 2/2002 | Maguire et al. |
| 6,625,992 B2 | | 9/2003 | Maguire et al. |
| 6,923,009 B2 | | 8/2005 | Kudaravalli |
| 2005/0016187 A1 | | 1/2005 | Kudaravalli |
| 2007/0214821 A1 | | 9/2007 | Astra |
| 2007/0245749 A1 | | 10/2007 | Atkins et al. |
| 2010/0016168 A1 | * | 1/2010 | Atkins .................. F25D 19/006 505/162 |
| 2011/0219810 A1 | * | 9/2011 | Longsworth ............. F25B 9/14 62/474 |
| 2012/0085121 A1 | | 4/2012 | Longsworth |
| 2012/0285181 A1 | | 11/2012 | Dunn et al. |
| 2013/0008190 A1 | | 1/2013 | Longsworth |
| 2013/0067952 A1 | * | 3/2013 | Ri ......................... F25B 25/005 62/513 |

FOREIGN PATENT DOCUMENTS

| | | | |
|---|---|---|---|
| CN | 102290187 A | | 12/2011 |
| EP | 2562489 A1 | | 2/2013 |
| JP | 57-58302 | | 4/1982 |
| JP | 58-112305 | | 7/1983 |
| JP | 1-269874 A | | 10/1989 |
| JP | 401269874 A | * | 10/1989 |
| JP | 5-126426 A | | 5/1993 |
| JP | 08-222429 A | | 8/1996 |
| JP | 08-279412 | | 10/1996 |
| JP | 11-63697 | | 3/1999 |
| JP | 11-063697 A | | 3/1999 |
| JP | 2000-506584 A | | 5/2000 |
| JP | 2003-139427 A | | 5/2003 |
| JP | 2005-28132 | | 2/2005 |
| WO | 97/33671 | | 9/1997 |
| WO | 2011/115790 A2 | | 9/2011 |
| WO | 2011/132231 A1 | | 10/2011 |
| WO | 2013/006299 A1 | | 1/2013 |

OTHER PUBLICATIONS

Korean Office Action dated Nov. 4, 2015 for the Corresponding Korean Patent Application No. 10-2015-7021208.
Japanese Office Action dated Jul. 12, 2016 for the Corresponding Japanese Patent Application No. 2015-552664.
Chinese Office Action dated Jun. 17, 2016 for the Corresponding Chinese Patent Application No. 201480004578.2.
German Office Action dated Mar. 30, 2016 for the Corresponding German Patent Application No. 11 2014 000 403.0.
German Office Action dated Jul. 17, 2017 for the Corresponding German Patent Application No. 11 2014 000 403.0.

* cited by examiner

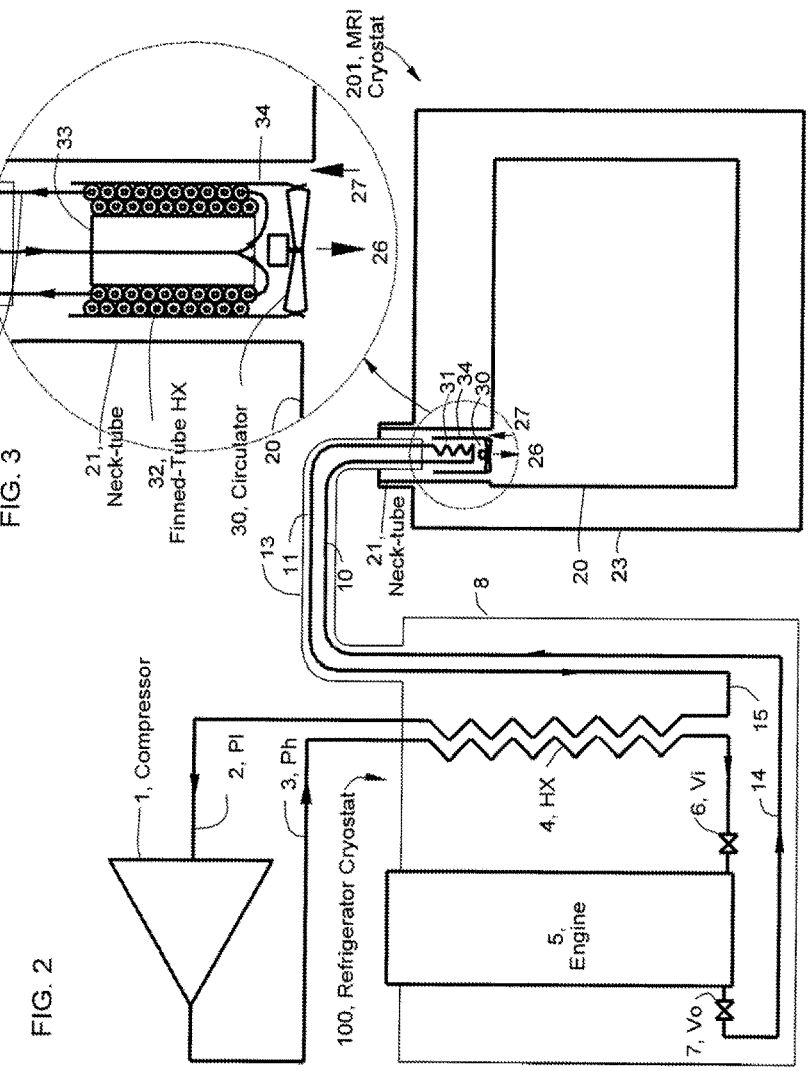

MRI COOL DOWN APPARATUS

BACKGROUND OF THE INVENTION

1. Field of the Invention

This invention relates to the cooling down of a superconducting magnet surrounded by a fluid at low pressure by a refrigerator circulating a fluid at a higher pressure.

2. Background Information

Superconducting magnets that are used in MRI cryostats and which operate in a bath of liquid helium are cooled down and tested in the factory before being shipped. It has been standard practice to leave enough helium in the magnet so that it stays cold during the three to five weeks it typically takes to get from the factory to the site where it will be used. Much of the helium boils off during transit and has to be replaced at the final site. The growing shortage of helium is motivating manufacturers to use different strategies to conserve helium. One strategy is to recover the helium from the magnet after it is tested and allow the magnet to warm up and be shipped warm. On site the magnet is then cooled down by a refrigerator that consists of a compressor external to a refrigerator cryostat in which helium is cooled then circulated through the magnet cryostat through vacuum jacketed transfer lines. A refrigerator that operates on the Brayton cycle has been developed to cool the magnet on site. It consists of a compressor that supplies gas at a discharge pressure of about 2 MPa to a counterflow heat exchanger, from which gas is admitted to an expansion space through an inlet valve, expands the gas adiabatically to about 0.8 MPa, exhausts the expanded gas (which is colder) through in outlet valve, circulates the cold gas through vacuum jacketed transfer lines to the magnet cryostat, then returns the gas through the counterflow heat exchanger to the compressor. An MRI cryostat that can be cooled by helium at pressures as high as 1 MPa has been developed recently. Most of the MRI magnets built to date though have been designed to operate with the helium at atmospheric pressure. 0.1 MPa, and to withstand a maximum pressure of about 0.2 MPa. The object of this invention is to provide a means to cool down a magnet that can only tolerate a pressure of less than 0.2 MPa with the output from a Brayton cycle refrigerator at about 0.8 MPa.

Patent Application Publication US 2011/0219810 filed Mar. 3, 2011 by R. C. Longsworth describes a reciprocating expansion engine operating on a Brayton cycle in which the piston has a drive stem at the warm end that is driven by a mechanical drive, or gas pressure that alternates between high and low pressures, and the pressure at the warm end of the piston in the area around the drive stem is essentially the same as the pressure at the cold end of the piston while the piston is moving. Patent Application Publication US 2012/0085121 filed Oct. 4, 2011 by R. C. Longsworth describes the control of a reciprocating expansion engine operating on a Brayton cycle, as described in the previous application, that enables it to minimize the time to cool an MRI magnet to cryogenic temperatures. Patent Application Publication US 2012/0285181 filed May 12, 2011 by S. Dunn et al describes means of controlling gas flow to the warm end of the Brayton cycle engine described in the 2011/0219810 application. These engines run on a Brayton cycle that is reasonably efficient operating at a high pressure of 2 MPa and a low pressure of 0.8 MPa but would not be very efficient if the low pressure were 0.1 MPa. The best way to use this type of engine is to have helium circulate in a second cooling circuit at about 0.1 MPa that transfers heat from the magnet to a heat exchanger cooled by the Brayton cycle refrigerator.

One approach to cooling down an MRI magnet using helium at about 0.1 MPa is described in U.S. Pat. No. 6,923,009 by Kudaravalli. This system comprises a circulator at room temperature, a counter-flow heat exchanger that precools the supply gas with the return gas, a heat exchanger cooled by liquid nitrogen, and lines that enable the cold gas to flow through the magnet. U.S. Pat. No. 6,347,522 by J. F. Maguire et al describes a system for cooling a remote thermal load comprising one or more refrigerators cooling one or more cold heat exchangers, a secondary circuit of helium at about 0.1 MPa that is cooled in the cold heat exchangers, a circulator in the secondary circuit which is in the refrigerator cryostat, and lines that enable the cold gas to flow through the remote thermal load, e.g. a magnet. U.S. Pat. No. 6,625,992 by J. F. Maguire et al is a continuation of the previous patent that removes the restriction that the circulator be in the refrigerator cryostat. Patent Application Publication US 2007/0214821 filed Mar. 16, 2007 by E. Astra describes an MRI magnet that has a refrigerator mounted in the neck tube of an MRI cryostat such that the cold end is in contact with helium gas that cools the magnet, cooled helium being circulated by natural convection or one of several types of fans. U.S. Pat. No. 5,461,873 by R. C. Longsworth describes a refrigerator that is mounted in the neck tube at the top of an MRI cryostat that has tubes arranged such that the magnet is cooled by natural convection. U.S. Pat. No. 4,484,458 by R. C. Longsworth describes a refrigerator that is mounted in the neck tube at the top of an MRI cryostat and has a finned-tube heat exchanger at the cold end which circulates helium by condensing it and having it drip down.

Cooling systems that use gaseous helium at near atmospheric pressure to cool superconducting MRI magnets or other objects can provide temperatures of 4.3 K or higher. Most MRI magnets today are kept cold, after they are cooled down, by a refrigerator in the neck tube, or parallel to the neck tube, that provides cooling of about 40 W at about 40 K plus about 1 W at 4.2 K. In contrast, the refrigerator that has been designed to cool down an MRI magnet using a Brayton cycle engine as described in Patent Application Publication US 2012/0285181 produces over 1,500 W of refrigeration at 250 K and over 500 W at 100 K. This refrigerator is too large to fit in the neck tube of an MRI cryostat however instead of delivering cold helium at 0.8 MPa to the magnet the cold helium can be circulated through a heat exchanger in the neck tube which can then be used to cool the helium in the magnet at about 0.1 MPa. The heat exchanger is inserted in the neck tube before cool down and removed after the MRI magnet has been cooled to about 50 K. If the neck tube is too small to contain the heat exchanger then it can be housed in a separate heat exchanger cryostat that is removeably inserted in the smaller neck tube.

SUMMARY OF THE INVENTION

This invention combines the high capacity of a Brayton cycle refrigerator operating at about 2/0.8 MPa with a coupling heat exchanger and circulator to cool a magnet with helium at about 0.1 MPa from room temperature to about 50 K. The coupling heat exchanger is a coil of finned-tubes in a sleeve that is arranged for the helium in the MRI cryostat to flow in a counterflow heat transfer relation with the helium from the refrigerator. Helium is forced through the heat exchanger by a variable flow circulator that maintains a near constant temperature difference between the helium from the Brayton cycle refrigerator and the helium that cools the magnet. The cold components of the refrigerator are contained in a refrigerator cryostat which is separated from the MRI cryostat by vacuum jacketed transfer lines. The heat exchanger and circulator are located at the MRI cryostat end of the transfer line in a removeable relationship with the MRI cryostat.

BRIEF DESCRIPTION OF THE DRAWINGS

FIG. 2 shows a Brayton cycle refrigerator circulating cold helium from the engine at about 0.8 MPa through vacuum jacketed transfer lines to a coupling heat exchanger in the neck tube of an MRI cryostat. A circulator which is also in the MRI cryostat drives helium which is at a pressure of about 0.1 MPa through the heat exchanger and MRI cryostat where it cools down a magnet.

FIG. 3 shows a preferred embodiment of the neck tube heat exchanger which is a two layer coil of finned-tubing.

DESCRIPTIONS OF THE PREFERRED EMBODIMENTS

The components that are shown in FIGS. 1-4 use the same number and the same diagrammatic representation to identify equivalent parts. Since cold gas is denser than warm gas most of the components are shown with the cold end down. Components that are at cryogenic temperatures, <125 K, are thermally insulated from the surrounding ambient by vacuum, <0.1 Pa, within a housing, the assembly being referred to as a cryostat. The present system has a cryostat for the cold refrigerator components, a cryostat for the cold MRI components, and an option of a cryostat for the cold coupling heat exchanger.

Figure 1:
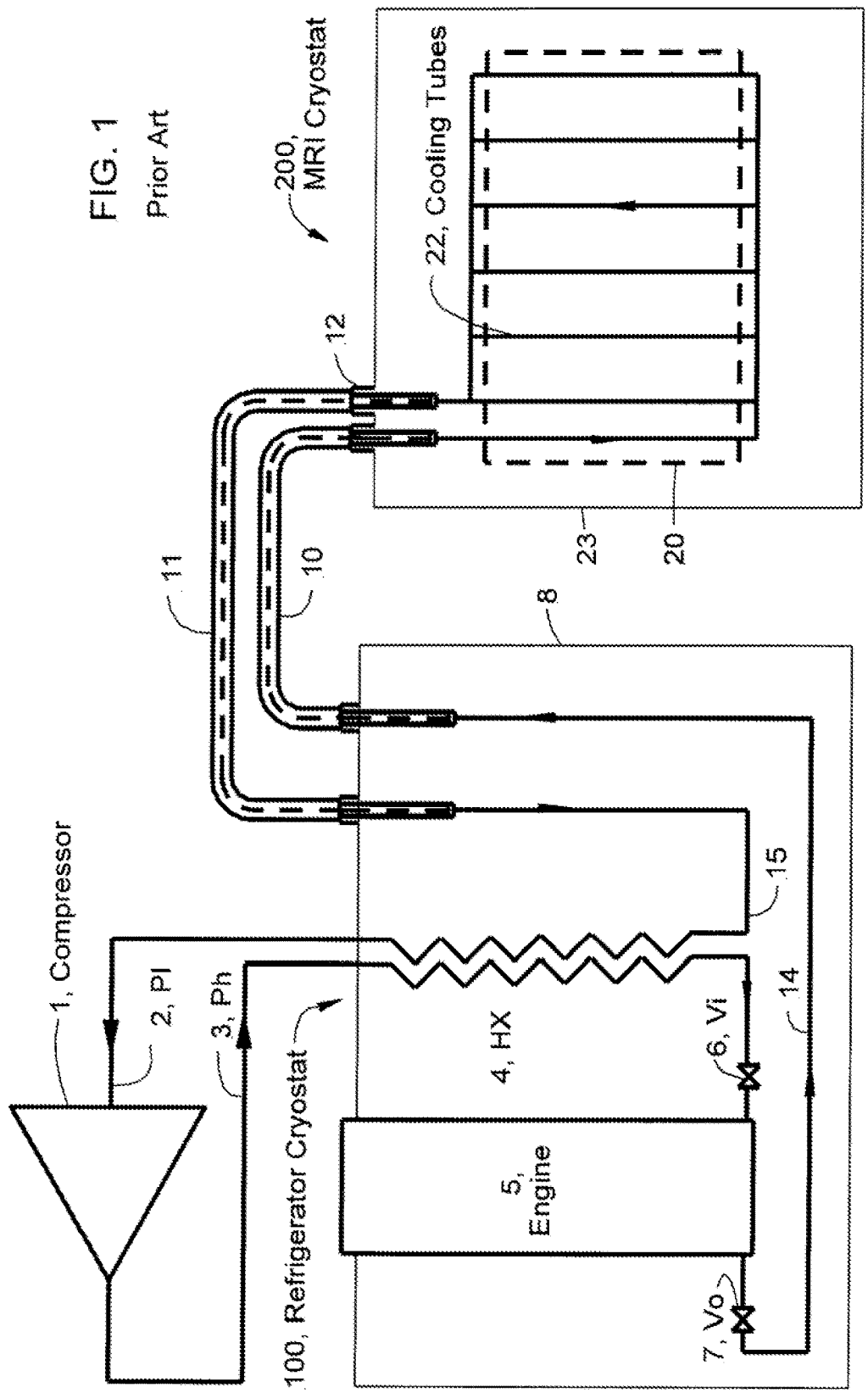
FIG. 1 shows the prior art of a Brayton cycle refrigerator circulating cold helium from the engine through vacuum jacketed transfer lines to an MRI cryostat where it flows through tubes at about 0.8 MPa to cool down a magnet.

FIG. 1 is a schematic of a prior art means of cooling down an MRI magnet consisting of a Brayton cycle refrigerator connected to MRI cryostat 200 by vacuum jacketed transfer lines 10 and 11. Helium at low pressure, Pl, about 0.8 MPa returns through line 2 to compressor 1 and is discharged at high pressure, Ph, about 2 MPa, in line 3. High pressure gas flows through heat exchanger, HX, 4 where it is cooled by returning low pressure gas from line 15 before flowing into expansion engine 5 through inlet valve, Vi, 6 then out through outlet valve, Vo, 7 into line 14. These cold components are contained in vacuum enclosure 8 and comprise refrigerator cryostat 100. MRI cryostat 200 comprises vacuum enclosure 23, magnet container 20, and cooling tubes 22. Cold helium from line 14 flows to cooling tubes 22 through vacuum jacketed transfer line 10, which has bayonet couplings 12 on each end, and from cooling tubes 22 to line 15 through vacuum jacketed transfer line 11, which also has bayonet couplings 12 on each end.

Cooling tubes 22 can withstand a pressure of up to 1 MPa which is more than the output pressure from Brayton engine 5.

Figure 4:
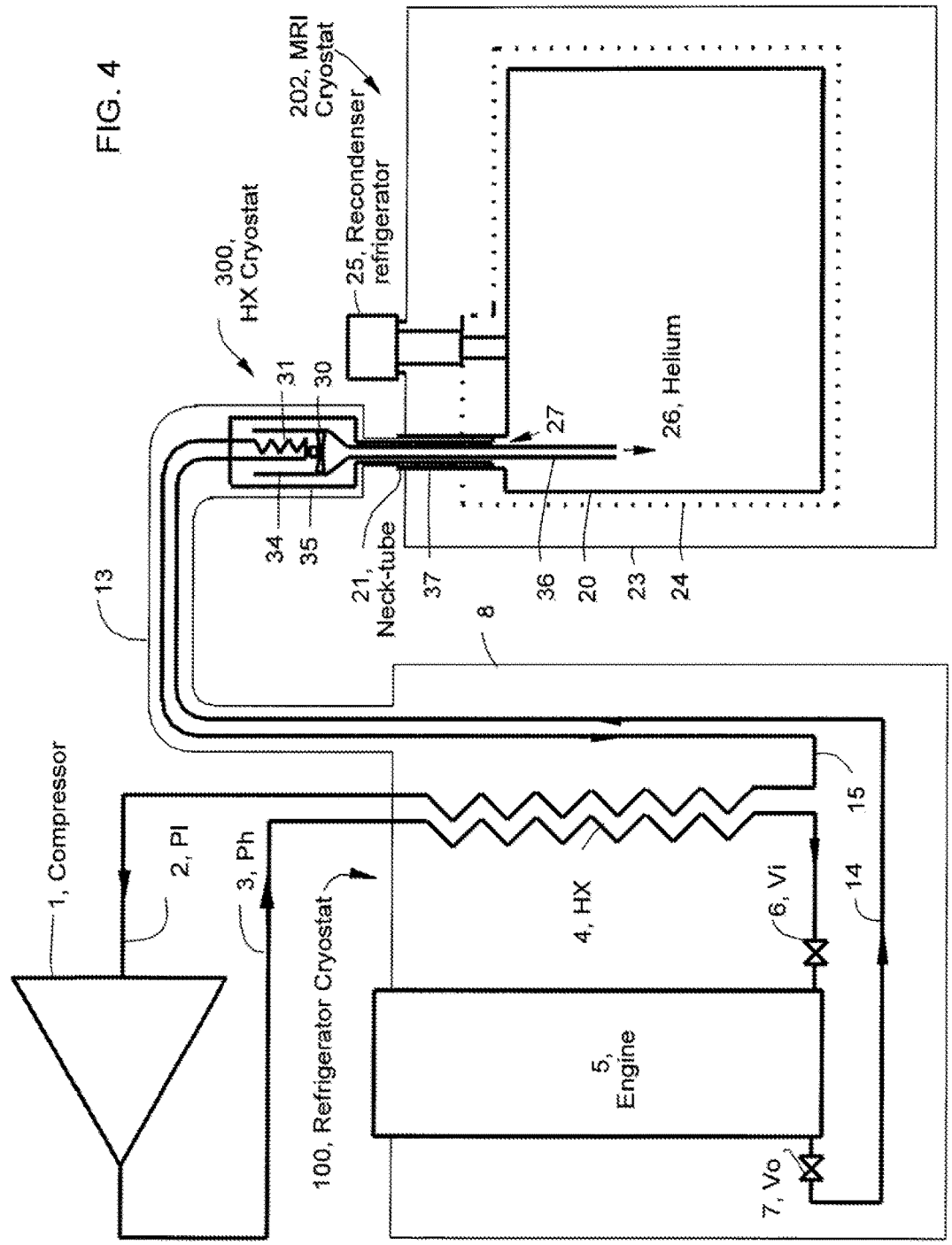
FIG. 4 shows a Brayton cycle refrigerator circulating cold helium from the engine at about 0.8 MPa through vacuum jacketed transfer lines to a heat exchanger in a cryostat that has an extension which fits in the neck tube of an MRI cryostat. A circulator which is also in the heat exchanger cryostat drives helium which is at a pressure of about 0.1 MPa through the heat exchanger and MRI cryostat where it cools down a magnet.

FIG. 2 is a schematic of the same Brayton refrigerator shown in FIG. 1 but the cold helium at about 0.8 MPa flows from transfer line 10 through coupling heat exchanger 31, which is in neck tube 21, then returns through transfer line 11 to refrigerator cryostat 100. Helium 26 after being cooled by heat exchanger 31, at a pressure of about 0.1 MPa, is circulated in magnet container 20 by circulator 30. Transfer lines 10 and 11 can be enclosed in separate vacuum jackets as shown in FIG. 1 or a common vacuum jacket 13 as shown in FIGS. 2 and 4. Coupling heat exchanger 31, sleeve 34, and circulator 30 are all connected to transfer lines 10 and 11 and their enclosure 13, and can be inserted and removed from neck tube 21.

The details of one possible configuration of coupling heat exchanger 31 is shown in FIG. 3 as finned-tube heat exchanger 32. Two separate coils in two layers of finned-tubes are shown coiled around mandrel 33 and within sleeve 34. Cold gas in line 14 from the Brayton cycle refrigerator enters the bottom end of each coil of finned-tubes and returns to line 15 from the top end of each coil. Helium 26 is drawn down through heat exchanger 32 by circulator 30 and is cooled in a counter flow heat transfer relation. This helium circulates around the MRI magnet and returns to neck tube 21 warmer. Helium 27 flows up through the annular gap between neck tube 21 and sleeve 34 to enter the top end of heat exchanger 32.

Table 1 provides an example of the heat transfer relations for a finned tube heat exchanger, 32, that has an outside diameter of 80 mm and length of 114 mm which has 5.5 g/s of helium flowing through the tubes from the Brayton cycle refrigerator and 5.0 g/s of helium at 0.15 MPa being circulated around the MRI magnet.

TABLE 1

| Example of Heat Exchanger performance, calculated | | |
| --- | --- | --- |
| T of He from MRI magnet, 27 - K | 300 | 93 |
| T of He to MRI magnet, 26 - K | 246 | 76 |
| T out of HX 32 in line 15 - K | 280 | 85 |
| T into HX 32 in line 14 - K | 231 | 70 |
| Cooling - W | 1,470 | 620 |
| Circulator 30 flow rate - g/s | 5.0 | 5.0 |
| Pressure drop through fins in HX 32 - kPa | 8.1 | 1.8 |

After the magnet has been cooled down, transfer lines 10 and 11 and heat exchanger 32 are removed from neck tube 21 and replaced with an expander the will keep the magnet cold. Expanders that are presently being used operate on a GM cycle and have a first stage diameter of about 100 mm. The neck tube diameter is somewhat greater.

FIG. 4 is a schematic that shows the same Brayton cycle refrigerator as shown in FIGS. 1 and 2 cooling down a magnet in MRI cryostat 202. In steady state the MRI magnet is cooled by refrigerator 25 which is not mounted in neck tube 21 but directly on vacuum housing 23 with the first stage of the refrigerator attached to warm shield 24 at about 40 K and the second stage attached to magnet container 20 at about 4.2 K. In this design neck tube 21 can have a diameter that is too small to accommodate coupling heat exchanger 31. This problem can be surmounted by putting heat exchanger 31 in a separate coupling heat exchanger cryostat 202 located above neck tube 21 and flowing cold helium 26 down through tube 36 which extends into magnet container 20. Helium 27, that has been warmed after cooling the magnet, flows to the top of heat exchanger 31, through the annular gap between tube 36 and the inner tube of bayonet 37, then between the outside of sleeve 30 and the inside of shell 35. The vacuum between the inner and outer walls of bayonet 37 extends up around shell 35 and is shown extending through tube 13 to the vacuum in refrigerator cryostat 100. Alternatively transfer lines 10 and 11 may have their own vacuum housings, as shown in FIG. 1, and cryostat 300 may also have a separate vacuum.

While the above description is of an MRI magnet and cryostat, it is used as an example of any object that is to be cooled down in a similar cryostat, such a cryostat is referred to as an object cryostat rather than an MRI cryostat. Other embodiments of coupling heat exchangers, such as a tube with pin-fins, are within the scope of the following claims.

What is claimed is:

1. An apparatus for cooling down an object to cryogenic temperatures, the apparatus comprising:
    a Brayton cycle refrigerator for outputting a first stream of cold helium at a first pressure, the Brayton cycle refrigerator comprising
        a compressor,
        an expansion engine, and
        a counter-flow heat exchanger;
    a refrigerator cryostat, the refrigerator cryostat housing at least the expansion engine and the counter-flow heat exchanger;
    coupling heat exchanger transferring heat from a second stream of helium at a second pressure to the first stream;
    a plurality of gas transfer lines placing in fluid communication the expansion engine, the refrigerator cryostat, and the coupling heat exchanger; and
    a circulator circulating the second stream through an object cryostat containing the object being cooled;
    wherein the coupling heat exchanger and the circulator are proximate to the object cryostat and removable from the object cryostat;
    wherein said coupling heat exchanger is a coil of one or more layers of finned tubing, said first stream flowing inside tubing of the finned tubing and said second stream flowing through fins of the finned tubing axially in a counter flow heat transfer relation.

2. An apparatus in accordance with claim 1, wherein the coupling heat exchanger is removably located in a neck tube of said object cryostat.

3. An apparatus in accordance with claim 1, wherein the object cryostat is an MRI cryostat.

4. An apparatus in accordance with claim 1, wherein said coupling heat exchanger is located in a coupling heat exchanger cryostat which is removably inserted in said object cryostat.

5. An apparatus in accordance with claim 1, said first pressure being at least three times greater than said second pressure.

6. An apparatus in accordance with claim 1, wherein the plurality of gas transfer lines comprises a vacuum jacketed transfer line, the vacuum jacketed transfer line transferring the first stream between the refrigerator cryostat and the object cryostat.

7. An apparatus in accordance with claim 6 wherein the first stream is at a pressure of greater than 0.6 MPa.

8. An apparatus in accordance with claim 6, wherein the vacuum jacketed transfer line has a smaller diameter than other lines of the plurality of gas transfer lines.

* * * * *